US010194892B2

(12) United States Patent
Melanson et al.

(10) Patent No.: US 10,194,892 B2
(45) Date of Patent: Feb. 5, 2019

(54) DETACHABLE ARTICULATING ENDOSCOPIC TOOL CARTRIDGE

(71) Applicant: KARL STORZ ENDOVISION, INC., Charlton, MA (US)

(72) Inventors: Jeffrey S. Melanson, Sturbridge, MA (US); Sabine Zahler, Veterstetten (DE)

(73) Assignee: Karl Storz Endovision, Inc., Charlton, MA (US)

(*) Notice: Subject to any disclaimer, the term of this patent is extended or adjusted under 35 U.S.C. 154(b) by 843 days.

(21) Appl. No.: 14/514,793

(22) Filed: Oct. 15, 2014

(65) Prior Publication Data

US 2016/0106404 A1 Apr. 21, 2016

(51) Int. Cl.
*A61B 17/00* (2006.01)
*A61B 17/29* (2006.01)

(52) U.S. Cl.
CPC ........ *A61B 17/00234* (2013.01); *A61B 17/29* (2013.01); *A61B 17/2909* (2013.01); *A61B 2017/00464* (2013.01); *A61B 2017/00473* (2013.01); *A61B 2017/00477* (2013.01); *A61B 2017/291* (2013.01); *A61B 2017/292* (2013.01); *A61B 2017/2931* (2013.01); *A61B 2017/2946* (2013.01)

(58) Field of Classification Search
CPC .............. A61B 17/00234; A61B 17/29; A61B 17/2909; A61B 2017/00464; A61B 2017/00473; A61B 2017/00477; A61B 2017/291; A61B 2017/292; A61B 2017/2931; A61B 2017/2946

USPC .................. 606/1, 205–208, 267; 128/107.1; 604/14; 81/3.29, 421; 408/1 BD
See application file for complete search history.

(56) References Cited

U.S. PATENT DOCUMENTS

| 1,271,319 A | 7/1918 | Hotsinpiller |
| 3,667,474 A | 6/1972 | Lapkin et al. |
| 3,896,793 A | 7/1975 | Mitsui et al. |
| 3,915,157 A | 10/1975 | Mitsui |
| 3,924,608 A | 12/1975 | Mitsui |
| 4,436,087 A | 3/1984 | Ouchi |
| 4,483,562 A | 11/1984 | Schoolman |
| 4,653,476 A | 3/1987 | Bonnet |
| 4,880,015 A | 11/1989 | Nierman |
| 4,949,706 A | 8/1990 | Thon |
| 4,950,273 A | 8/1990 | Briggs |
| 5,025,778 A | 6/1991 | Silverstein et al. |
| 5,037,433 A | 8/1991 | Wilk et al. |

(Continued)

FOREIGN PATENT DOCUMENTS

| DE | 4332497 A1 | 3/1995 |
| DE | 19820486 A1 | 11/1998 |

(Continued)

OTHER PUBLICATIONS

EP Extended Search Report Application No. 15189667.7 dated Mar. 4, 2016 Completed: Feb. 24, 2016 9 Pages.

*Primary Examiner* — Gary Jackson
*Assistant Examiner* — Zahed Kabir
(74) *Attorney, Agent, or Firm* — Whitmyer IP Group LLC

(57) ABSTRACT

A medical instrument is provides that includes a handle, a shaft, and a tool insert. The tool insert is attachable to the shaft by a threaded connection which engages a slot connection and to the handle and by a retaining member for actuation of the tool.

21 Claims, 9 Drawing Sheets

(56) References Cited

U.S. PATENT DOCUMENTS

| | | | |
|---|---|---|---|
| 5,254,130 A | 10/1993 | Poncet et al. | |
| 5,259,366 A | 11/1993 | Reydel et al. | |
| 5,308,358 A | 5/1994 | Bond et al. | |
| 5,312,391 A | 5/1994 | Wilk | |
| 5,312,434 A | 5/1994 | Crainich | |
| 5,318,528 A | 6/1994 | Heaven et al. | |
| 5,330,502 A | 7/1994 | Hassler et al. | |
| 5,344,428 A | 9/1994 | Griffiths | |
| 5,353,784 A | 10/1994 | Nady-Mohamed | |
| 5,386,818 A | 2/1995 | Schneebaum et al. | |
| 5,454,827 A | 10/1995 | Aust et al. | |
| 5,474,057 A | 12/1995 | Makower et al. | |
| 5,483,951 A | 1/1996 | Frassica et al. | |
| 5,503,616 A | 4/1996 | Jones | |
| 5,569,164 A | 10/1996 | Lurz | |
| 5,582,609 A | 12/1996 | Swanson et al. | |
| 5,609,601 A | 3/1997 | Kolesa et al. | |
| 5,624,398 A | 4/1997 | Smith et al. | |
| 5,630,782 A | 5/1997 | Adair | |
| 5,637,110 A * | 6/1997 | Pennybacker | A61B 18/1445 606/170 |
| 5,674,181 A | 10/1997 | Iida | |
| 5,735,849 A | 4/1998 | Baden et al. | |
| 5,749,889 A | 5/1998 | Bacich et al. | |
| 5,766,196 A | 6/1998 | Griffiths | |
| 5,782,834 A | 7/1998 | Lucey et al. | |
| 5,820,546 A | 10/1998 | Ouchi | |
| 5,827,177 A | 10/1998 | Oneda et al. | |
| 5,833,656 A | 11/1998 | Smith et al. | |
| 5,885,207 A | 3/1999 | Iwasaka | |
| 5,893,875 A * | 4/1999 | O'Connor | A61B 17/29 606/167 |
| 5,904,647 A | 5/1999 | Ouchi | |
| 5,906,630 A * | 5/1999 | Anderhub | A61B 10/06 606/153 |
| 5,921,915 A | 7/1999 | Aznoian et al. | |
| 5,938,678 A | 8/1999 | Zirps et al. | |
| 5,954,692 A | 9/1999 | Smith et al. | |
| 5,964,717 A * | 10/1999 | Gottlieb | A61B 10/06 600/567 |
| 5,993,461 A | 11/1999 | Abae | |
| 5,995,875 A | 11/1999 | Blewett et al. | |
| 6,001,114 A * | 12/1999 | Ouchi | A61B 17/29 606/167 |
| 6,059,719 A | 5/2000 | Yamamoto et al. | |
| 6,066,090 A | 5/2000 | Yoon | |
| 6,071,233 A | 6/2000 | Ishikawa et al. | |
| 6,106,521 A | 8/2000 | Blewett et al. | |
| 6,179,776 B1 | 1/2001 | Adams et al. | |
| 6,227,782 B1 | 5/2001 | Bowling et al. | |
| 6,296,635 B1 | 10/2001 | Smith et al. | |
| 6,352,503 B1 | 3/2002 | Matsui et al. | |
| 6,409,727 B1 | 6/2002 | Bales et al. | |
| 6,482,198 B1 | 11/2002 | Overaker et al. | |
| 7,029,435 B2 | 4/2006 | Nakao | |
| 7,060,024 B2 | 6/2006 | Long et al. | |
| 7,070,602 B2 | 7/2006 | Smith et al. | |
| 7,815,658 B2 * | 10/2010 | Murakami | A61B 17/32009 604/22 |
| 7,862,553 B2 * | 1/2011 | Ewaschuk | A61B 17/29 604/264 |
| 2002/0128682 A1 | 9/2002 | Prestel et al. | |
| 2003/0236549 A1 | 12/2003 | Bonadio et al. | |
| 2005/0101879 A1 * | 5/2005 | Shidham | A61B 10/0283 600/566 |
| 2005/0113640 A1 | 5/2005 | Saadat et al. | |
| 2005/0234297 A1 | 10/2005 | Devierre et al. | |
| 2007/0167679 A1 | 7/2007 | Miyamoto et al. | |
| 2007/0167680 A1 | 7/2007 | Miyamoto et al. | |
| 2007/0250113 A1 * | 10/2007 | Hegeman | A61B 1/0055 606/207 |
| 2007/0260273 A1 | 11/2007 | Cropper et al. | |
| 2008/0269557 A1 | 10/2008 | Marescaux et al. | |
| 2008/0269562 A1 | 10/2008 | Marescaux et al. | |
| 2009/0182366 A1 * | 7/2009 | Kennedy | A61B 17/32053 606/170 |
| 2009/0209946 A1 * | 8/2009 | Swayze | A61B 17/0682 606/1 |
| 2009/0299141 A1 * | 12/2009 | Downey | A61B 17/2909 600/118 |
| 2013/0237907 A1 * | 9/2013 | Bacher | A61B 17/2909 604/95.04 |
| 2017/0119421 A1 * | 5/2017 | Staunton | A61B 17/32002 |

FOREIGN PATENT DOCUMENTS

| | | |
|---|---|---|
| DE | 202014004160 | 6/2014 |
| EP | 2522285 A1 | 11/2012 |
| GB | 2325166 A | 11/1998 |
| JP | 10305037 A | 11/1998 |
| JP | 2002503131 T | 1/2002 |
| WO | 9724072 A1 | 7/1997 |
| WO | 9856297 A1 | 12/1998 |
| WO | 0207611 A2 | 1/2002 |
| WO | 2005044095 A1 | 5/2005 |
| WO | 2006046263 A1 | 5/2006 |
| WO | 2006052927 A2 | 5/2006 |
| WO | 2006110275 A2 | 10/2006 |
| WO | 2007080974 A1 | 7/2007 |
| WO | 2007104397 A1 | 9/2007 |

* cited by examiner

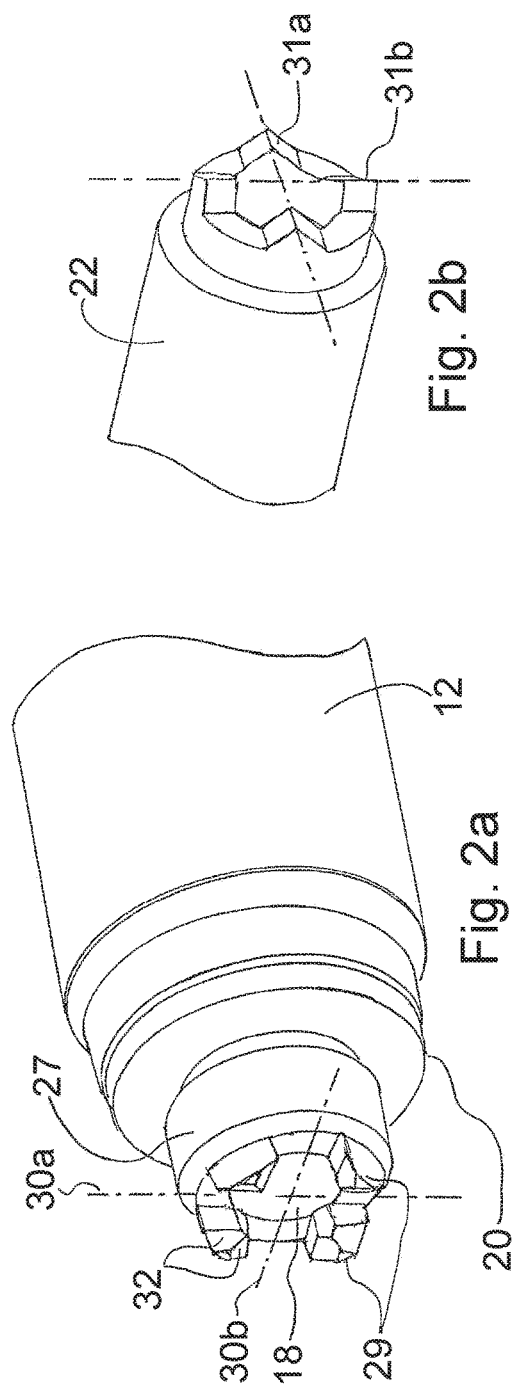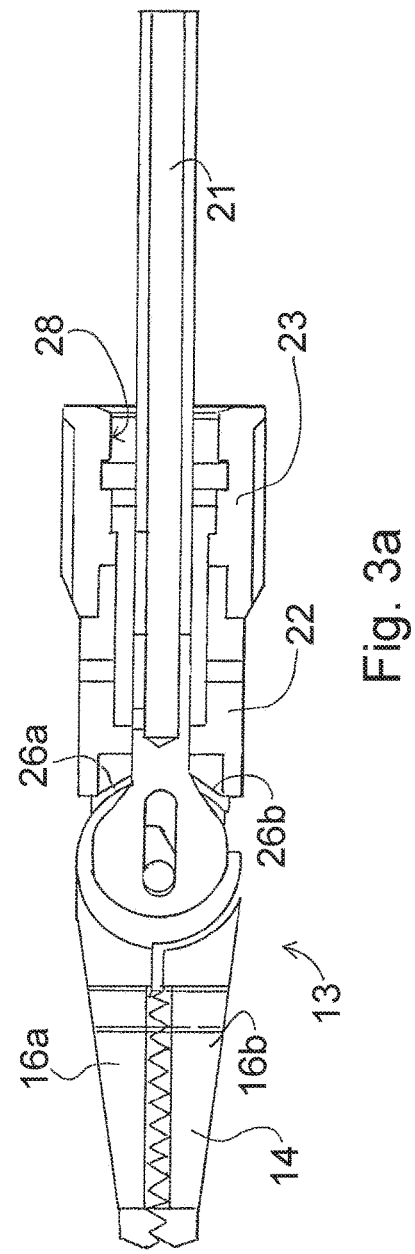

DETACHABLE ARTICULATING ENDOSCOPIC TOOL CARTRIDGE

FIELD OF THE INVENTION

The present invention relates to a medical instrument. In particular, the present invention relates to endoscopic surgical instruments useful in such surgical techniques as transluminal or transgastric surgery.

BACKGROUND OF THE INVENTION

Endoscopic surgery has long been known as an effective technique for accomplishing surgical tasks in a minimally-invasive manner. This surgical technique, which utilizes small surgical tools advanced to a surgical site via small incisions in the patient's body, has significantly reduced the drawbacks of traditional open cavity surgery.

Somewhat more recently, transluminal/transgastric surgery has reduced the negative drawbacks of surgical intervention even further. Transluminal surgery utilizes one or more natural body orifices to introduce surgical instruments and equipment in order to minimize incisions. In transgastric surgery, for example, a surgical instrument is inserted into the patient's mouth and fed to the patient's stomach. The wall of the patient's stomach can then be punctured so that the instrument can access other parts of the patient's abdomen. An incision in the wall of the stomach is preferable to external incisions because there are no nerve endings in the stomach. Transgastric endoscopic surgery reduces patient pain and recovery time as well as the risk of infection.

Transluminal/transgastric surgery requires the use of surgical tools that can manipulate body tissue inside the patient's largely closed body cavity by a surgeon's hands outside of the body. Surgical tools appropriate for these surgical techniques traditionally have a handle for manipulating a tool portion that is located on an opposite end of an elongated middle portion.

In many transluminal/transgastric surgical systems, a primary instrument is inserted into the body and advanced to the surgical site. The primary instrument typically has one or more channels for inserting surgical tools, an optical channel, one or more light channels, and/or one or more channels for evacuation or insufflation. The overall size of the primary instrument is restricted, however, by the size limitations of the human body. This size restriction on the primary instrument limits the number of channels that can be used for surgical tools, etc. As a result it is often necessary to swap the tools inserted in the primary instrument and being used in a surgery during the surgery, sometimes multiple times. This requires that the tools be quickly accessible and swappable.

Next, surgical equipment for endoscopic surgery—especially transluminal/transgastric surgery—is precise, highly engineered equipment. Such equipment is expensive to acquire and to maintain. As a result, it can be cost intensive to provide surgeons with a full complement of the tools he or she might need to accomplish the surgical tasks typically encountered in a hospital or clinic.

What is needed therefore, is a medical instrument that enables a surgeon to quickly and safely swap surgical tools for use during an endoscopic surgery. What is also needed is a medical instrument that enables the reduction of repetitive equipment while still providing a full complement of surgical tools.

SUMMARY OF THE INVENTION

It is an object of the present invention to provide a medical instrument in which a tool portion can be rapidly and safely swapped for use during surgery.

It is a further object of the present invention to provide a medical instrument that reduces the amount of medical equipment that a user must acquire and maintain while not compromising the number tools available to the user.

These and other objects are accomplished by provision of a first embodiment of the present invention, a medical instrument that comprises: a shaft, comprising a threaded portion on a distal end thereof; a handle connected to the shaft; and a tool insert receivable in the shaft. The tool insert, comprises a tool portion, a collar rotatable relative to the tool insert comprising threads that correspond to the threaded portion of the shaft; and an elongated member for engagement with the handle for actuation of the tool portion.

In some embodiments, the shaft of the medical instrument further comprises at least one slot on its distal end and the tool portion includes at least one protrusion for engagement with the at least one slot to substantially prevent rotation of the tool portion relative to the shaft. In some embodiments, the shaft of the medical instrument further comprises two slots formed between four protrusions on the distal end of the shaft. In some embodiments, the medical instrument further comprises that each protrusion includes at least one surface inclined at an angle relative to the longitudinal axis of the shaft at its distal end.

In some embodiments, the tool insert further comprises a ball attached at a distal end of the elongated member for engaging with the handle and the handle further comprising an opening for engaging with the ball. In some embodiments, the opening is a keyhole opening for accepting and retaining the ball that is moveable between a retaining position and an accepting position. In some embodiments, the handle of the medical instrument further comprises an actuation assembly which receives a distal end of the elongated member and in which the keyhole opening is disposed, and wherein the keyhole opening is moveable in a direction perpendicular to the longitudinal axis of the portion of the elongated member disposed in the actuation assembly. In some embodiments, the keyhole opening is biased in the retaining position.

In some embodiments, the shaft of the medical instrument further comprises a rotation member on its proximal end for rotating the shaft and the tool insert relative to the handle, the rotation member being moveable along the longitudinal axis of the shaft at the portion of the shaft that is connected to the handle.

According to another embodiment of the present invention, a medical instrument is provided that comprises: a shaft, a handle connected to said shaft, and a tool insert receivable in the shaft. The handle comprises a retaining member that includes an opening and is moveable between a retaining position and an accepting position. The tool insert comprises a tool portion and an elongated member including a ball on a proximal end thereof for engaging with the opening. The retaining member permits the handle to exert force on the elongated member along a longitudinal axis thereof for actuation of the tool portion.

In some embodiments, the handle of the medical instrument further comprises an actuation assembly in which the retaining member is disposed and which receives the proximal end of the elongated member and wherein the retaining member is moveable in a direction perpendicular to the longitudinal axis of the portion of the elongated member disposed in the actuation assembly. In some embodiments, the opening is a keyhole opening including an accepting portion sized larger than the ball and a retaining portion sized smaller than the ball. In some embodiments, the medical instrument further comprises that when the retaining member is in the retaining position, the retaining portion of the opening is aligned with the longitudinal axis of the portion of the elongated member disposed in the actuation assembly and that when the retaining member is in the accepting position, the accepting portion is aligned with the longitudinal axis of the portion of the elongated member disposed in the actuation assembly. In some embodiments, the retaining member is a rod and is biased in the retaining position.

In some embodiments, the shaft of the medical instrument further comprises a threaded portion on a distal end thereof and wherein the tool insert further comprises a collar rotatable relative to the tool insert comprising threads that correspond to the threaded portion of the shaft. In some embodiments, the shaft of the medical instrument further comprises at least one slot on its distal end and the tool portion includes at least one protrusion for engagement with the at least one slot to substantially prevent rotation of the tool portion relative to the shaft. In some embodiments, the shaft of the medical instrument further comprises two slots formed between four protrusions on the distal end of the shaft.

According to another embodiment of the present invention, a medical instrument is provided that comprises a shaft, a handle connected to the shaft, and a tool insert receivable in the shaft. The handle comprises a threaded portion on a distal end thereof and a retaining member that includes an opening and that is moveable between a retaining position and an accepting position. The tool insert comprises a tool portion, a collar rotatable relative to the tool insert comprising threads that correspond to the threaded portion of the shaft, and an elongated member including a ball on a proximal end thereof for engaging with the opening. The retaining member permits the handle to exert force on the elongated member along a longitudinal axis thereof for actuation of the tool portion.

In some embodiments, the shaft of the medical instrument further comprises at least one slot on its distal end and the tool portion includes at least one protrusion for engagement with the at least one slot to substantially prevent rotation of the tool portion relative to the shaft. In some embodiments, the shaft of the medical instrument further comprises two slots formed between four protrusions on the distal end of the shaft. In some embodiments, each protrusion includes at least one surface inclined at an angle relative to the longitudinal axis of the shaft at its distal end.

In some embodiments, the handle of the medical instrument further comprises an actuation assembly in which the retaining member is disposed and which receives the proximal end of the elongated member and wherein the retaining member is moveable in a direction perpendicular to the longitudinal axis of the portion of the elongated member disposed in the actuation assembly. In some embodiments, the opening is a keyhole opening including an accepting portion sized larger than the ball and a retaining portion sized smaller than the ball. In some embodiments, the medical instrument further comprises that when the retaining member is in the retaining position, the retaining portion of the opening is aligned with the longitudinal axis of the portion of the elongated member disposed in the actuation assembly and wherein when the retaining member is in the accepting position, the accepting portion is aligned with the longitudinal axis of the portion of the elongated member disposed in the actuation assembly. In some embodiments, the retaining member is a rod and is biased in the retaining position.

Other objects, features, and advantages will be apparent from the following detailed description of embodiments of the present invention taken in conjunction with the accompanying drawings.

BRIEF DESCRIPTION OF THE DRAWINGS

FIG. 2a is a perspective close-up view of a part of the embodiment of FIG. 1.

FIG. 2b is a perspective close-up view of a part of the embodiment of FIG. 1.

FIGS. 3a-3b are cut-away views of a part of the embodiment of FIG. 1.

DETAILED DESCRIPTION OF THE INVENTION

Figure 1:
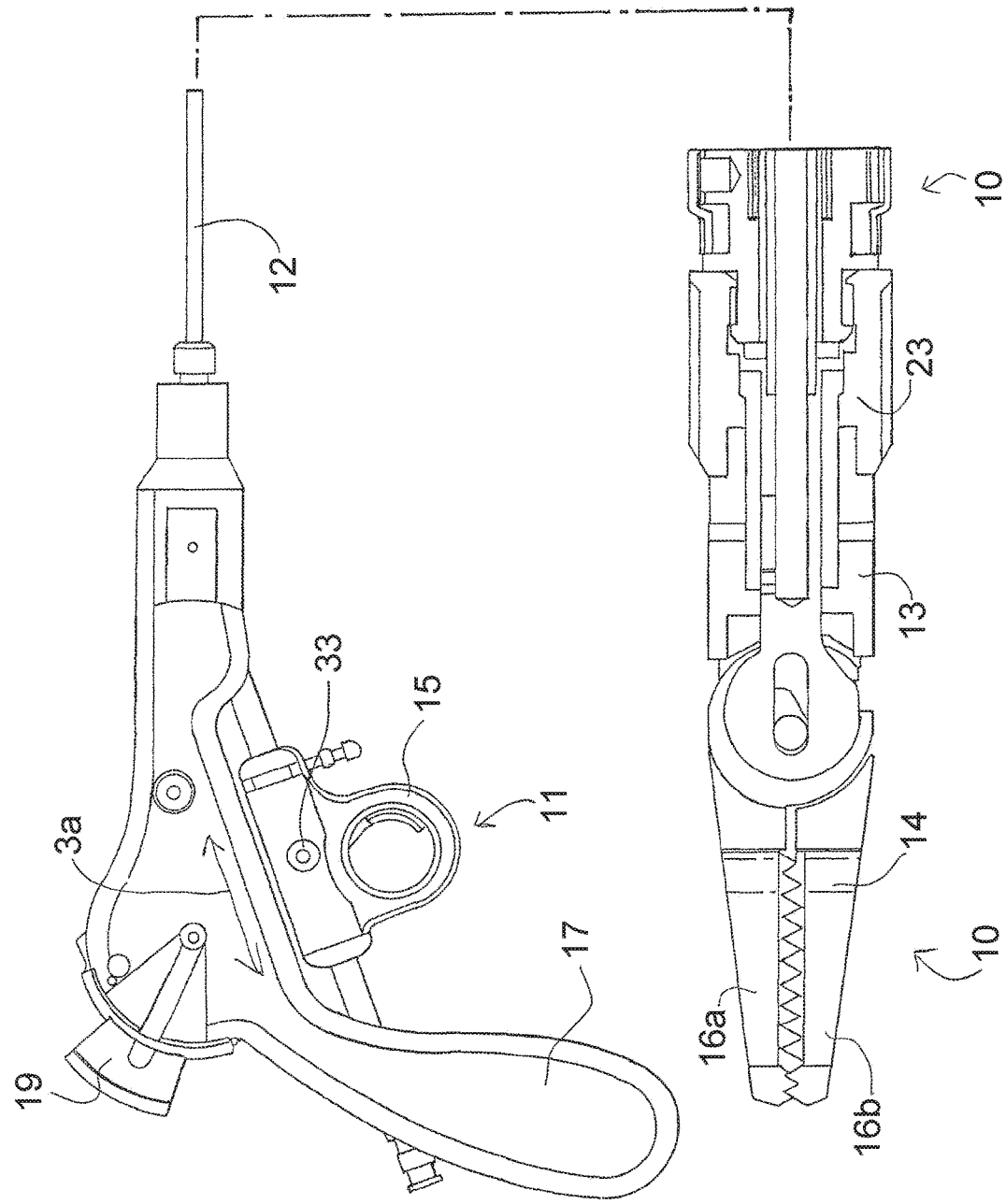
FIG. 1 is a side view of a first embodiment of the present invention.

The invention will now be described in reference to the drawings, which show embodiments of the present invention. FIG. 1 shows an endoscopic surgical instrument 10 according to one exemplary embodiment of the present invention. The surgical instrument 10 includes a handle portion 11 and a shaft 12. The shaft 12 holds a tool insert 13 which has a tool portion 14 on its distal end.

The handle portion 11 of the surgical instrument 10 is ergonomically designed for comfortable use by a surgeon. In some embodiments, the handle portion 11 is designed symmetrically so that it is comfortably grasped and operated by either a left hand or a right hand. This feature allows a surgeon to use two surgical instruments 10 simultaneously.

The handle portion 11 includes control mechanisms for the functions of the surgical instrument 10. In the embodiment shown, the actuation assembly 15 controls the actuation of the tool portion 14. In the embodiment shown in FIG. 1, the tool portion 14 is a grasper-type tool for securely grasping and holding tissue or other materials or objects between its two movable jaw members 16a and 16b. The jaw members 16a and 16b are moved by moving the assembly 15 relative to the grip 17, and the assembly 15 has a ring portion for receiving a finger of the surgeon.

Handle portion 11, in the embodiment shown in FIG. 1, further includes an articulation control 19 which is used to control the articulation of a distal region of the shaft 12.

The tool insert 13 is designed to be easily separable from the instrument 10 so that a plurality of tool inserts having a plurality of different types of tool portions can be used with a single instrument. This system requires simple and easy to use connections between the tool insert and the instrument.

FIG. 2a shows a close-up view of the distal end 20 of the shaft 12 of the instrument 10 shown in FIG. 1. The shaft 12 has a hollow channel 18 along its length for receiving an elongated part of the tool insert 13 as described below. The shaft 12 is made of flexible, biocompatible material and is designed and constructed to be highly resistant to twisting along its length. In most embodiments of the present invention the shaft 12 is flexible and resilient to radial forces, yet substantially incompressible or deformable when subjected to axial forces. These features allow for the surgical instrument to be easily inserted into a primary transluminal/transgastric surgical apparatus and for the surgeon to effectively use pushing or pulling forces with the surgical instrument.

In some embodiments, the shaft 12 and remainder of the instrument 10 include features that permit controlled articulation of the distal end of the shaft. Examples of such features are included in U.S. Pat. No. 8,137,263, the content of which is hereby incorporated by reference herein.

Figure 3B:
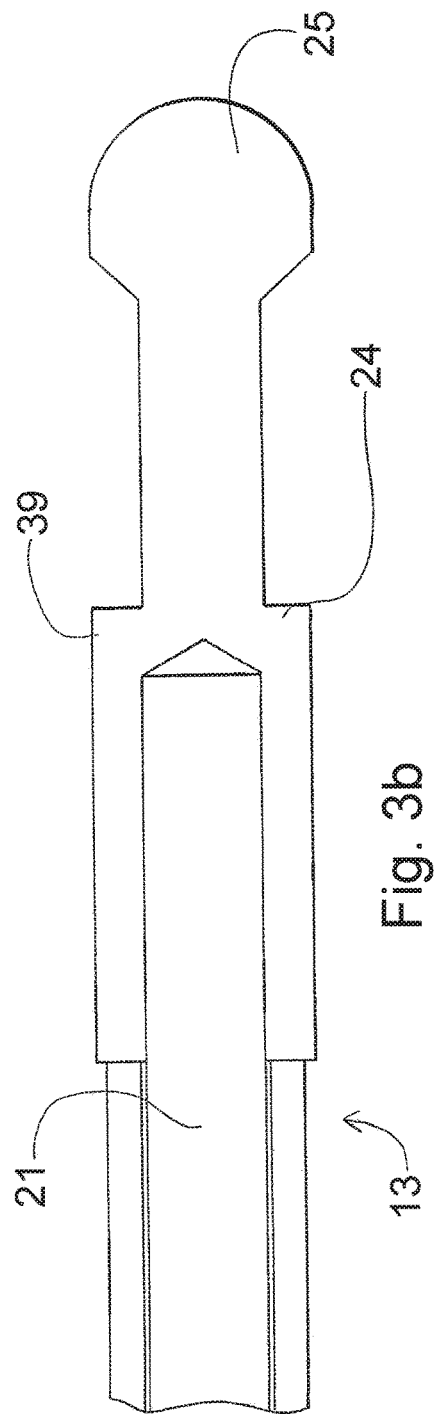
Figure 4:
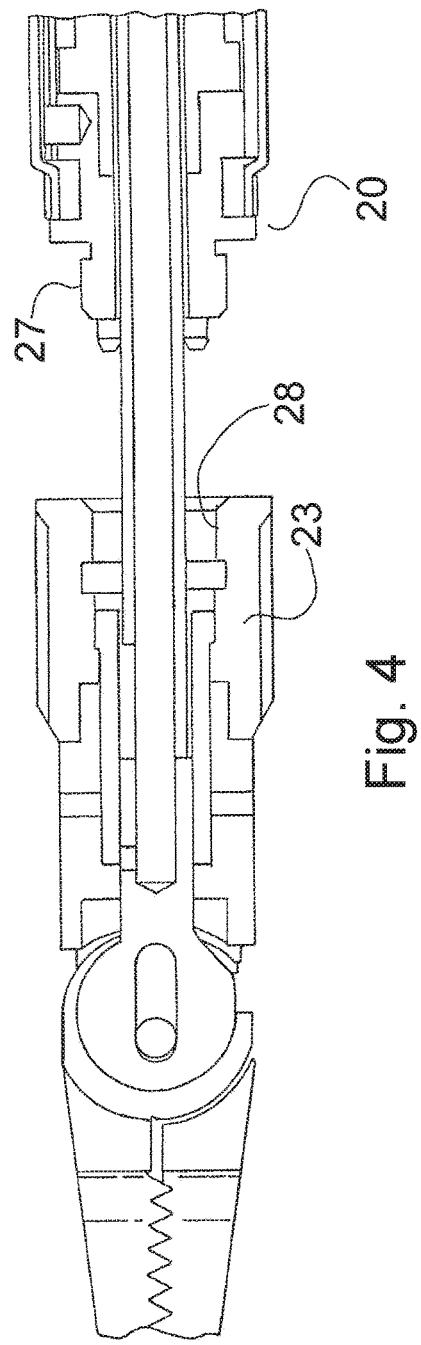
FIG. 4 is a cutaway view of a part of the embodiment of FIG. 1.

FIGS. 3a and 3b show in more detail the structure of a tool insert 13 according to the first exemplary embodiment of the present invention. FIG. 3a shows the distal end of the insert 13, where the tool portion 14 is attached. The tool portion 14 is attached to an elongated member 21, which is in the form of a wire in the embodiment shown in FIGS. 3a and 3b. The tool insert also includes a bearing 22 on the proximal side of the tool portion 14, and a collar 23 on the proximal side of the bearing 22.

The proximal end 24 of the tool insert 13 is shown in FIG. 3b. The proximal end includes a structure for engaging with the handle 11 of the instrument 10 so that a pulling and/or pushing force can be imparted to the elongated member 21 by the surgeon manipulating the handle 11. In the embodiment shown in FIG. 3b, the structure for engaging with the handle 11 is a ball 25, which permits a pulling and/or pushing force to be imparted to the tool insert.

In operation, when the ball 25 is pulled, the elongated member 21 pulls the tool portion 14 against the bearing 22. As described more fully below, the bearing 22 is secured against movement relative to the shaft 12 by the collar 23. The movement of the tool portion 14 against the bearing causes the jaw members 16a and 16b to open due to the force on the inclined surfaces 26a and 26b.

In order to secure the distal end of the tool insert 13, a threaded connection is used between the distal end 20 of the shaft 12 and the collar 23 of the tool insert 13. In the embodiment shown in FIGS. 1-4, a threaded surface 27 faces outwardly on the distal end 20 of the shaft 12. Threaded surface 27 corresponds to a threaded surface 28 on the collar 23. The collar 23 is free to rotate relative to the other parts of the tool insert 13 so that it can be threaded onto the threaded surface 27 and secured there.

The embodiment shown in FIGS. 1-4 also includes features to prevent the tool insert 13 from rotating relative to the shaft 12. The distal end 20 of the shaft 12 includes four protrusions 29 that are arranged to create two perpendicular slots. The slots are indicated by the dashed lines 30a and 30b shown in FIG. 2. One or more protrusions on the distal end of the bearing 22 are arranged to engage with these slots. As shown in FIG. 2b, the bearing 22 has, on its distal-facing end, two sets of two protrusions 31a and 31b that correspondent to the slots 30a and 30b. When the collar 23 is threaded down onto the distal end of the shaft, the protrusions 31 mate with the slots 30 and prevent rotation of the bearing 22 (and, thus, the entirety of the tool insert 13) relative to the shaft 12. In other embodiments, only one set of protrusions 31 is used and, likewise, in other embodiments, only one slot 30 is used on the shaft 12.

In the embodiment shown in FIGS. 2a and 2b, each of the protrusions 29 have inclined surfaces to make acceptance of the protrusions 31 into the slots 30 easier. The inclined surfaces 32 are set at an angle relative to the longitudinal axis of the shaft 12 at the distal end 20. Although the shaft 12 is flexible in some embodiments such that its longitudinal axis is not fixed along the entire length of the shaft, the longitudinal axis at the distal end 20 of the shaft can be easily defined as the axis that is normal to the plane that is perpendicular to the distal end 20 of the shaft 12.

The inclined surfaces 32 assist when the protrusions 31 of the bearing 22 are brought together with the protrusions 29 in an orientation in which the protrusions 31 are not aligned with the slots 30. In such a situation, the inclined surfaces 32 will exert a radial force on the bearing 22 to twist it into proper alignment with the slots 30.

In some embodiments, including the embodiment shown in FIG. 2b, the protrusions 31 on the bearing 22 also comprise inclined surfaces to make engagement with the slots on the shaft 12 easier.

FIG. 1 shows a cross section of the distal end of the tool insert 13 and the shaft 12, in which the insert 13 is seated on the shaft. The collar 23 is fully threaded via threaded surface 28 onto threaded shaft surface 27 such that the protrusions 31 on the bearing 22 are seated in the slots 30a and 30b on the distal end of the shaft 12. In this condition, the tool insert 13 is fixed in a longitudinal direction with respect to the shaft as well as prohibited from rotating relative to the shaft.

Figure 5:
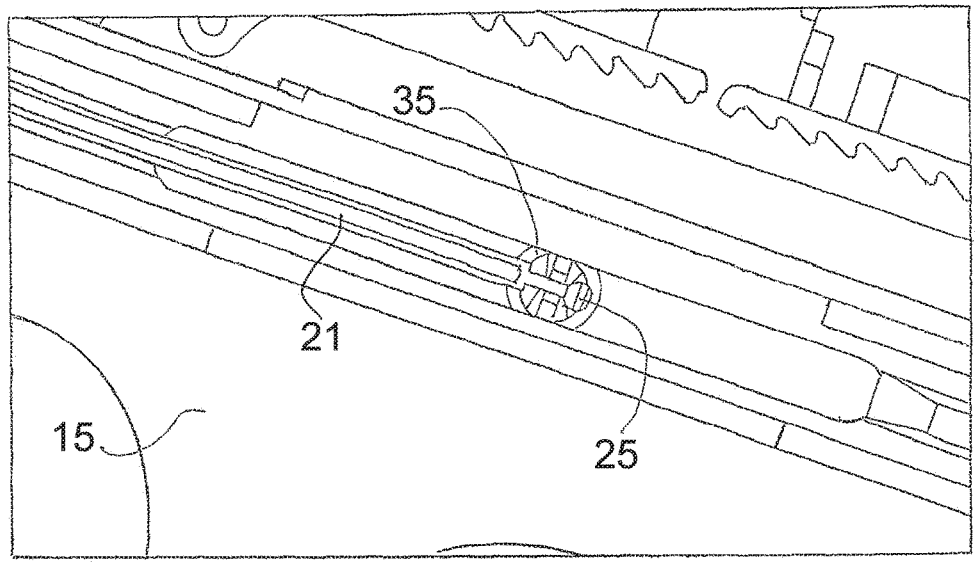
FIG. 5 is a close-up, cut-away view of a part of the embodiment of FIG. 1.

FIG. 5 shows a cut-away view of the actuation assembly 15 of the handle 11 of the instrument 10. In the embodiment shown, the actuation assembly 15 is adapted to engage the proximal end 24 of the tool insert 13. A button 33 is disposed on the outside of the assembly 15 for easy access by a user of the instrument 10 (See FIG. 1). The button 33 operates the structure of the assembly 15 that engages the tool insert 13. This structure, indicated generally in FIG. 5 by reference number 34, includes a retaining member that directly engages with the proximal end (the ball 25) of the tool insert.

Figure 6:
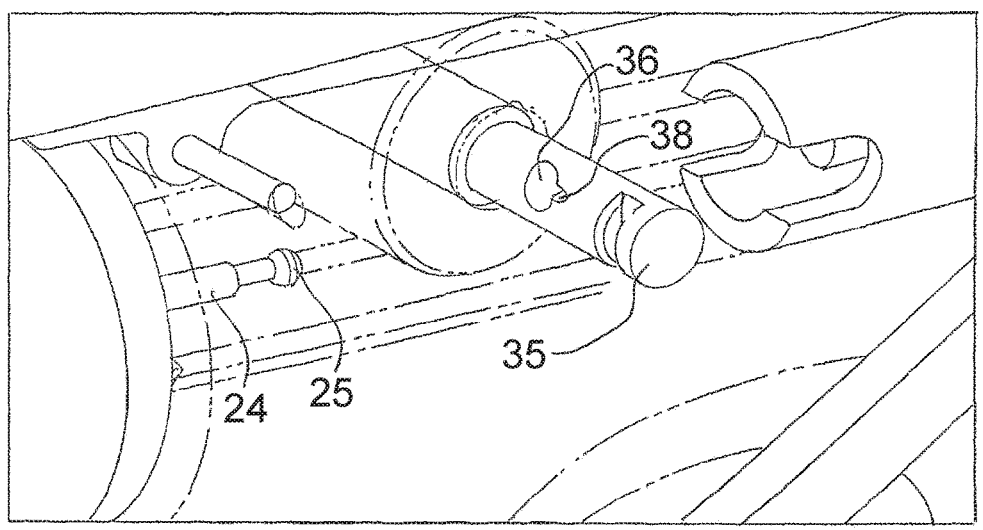
FIG. 6 is a close-up, cut-away view of a part of the embodiment of FIG. 1.

FIG. 6 shows an isometric cut-away view of the actuation assembly 15, including the retaining member 35. In this embodiment, the retaining member 35 is in the form of a rod that is oriented perpendicularly to the longitudinal axis of the proximal end 24 of the tool insert 13 when the tool insert is disposed in the assembly 15. The proximal end 24 of the tool insert 13 can be seen in FIG. 5 approaching the retaining member 35.

In the embodiment shown in FIG. 6, the retaining member 35 includes an opening 36 through which the proximal end 24 is received. In this embodiment, the opening 36 is in the form of a keyhole slot. The opening has an accepting portion 37, which is large enough that the ball 25 can pass through it, and a retaining portion 38, which is smaller than the accepting portion 37 so that the ball 25 cannot pass through it but is large enough to accommodate the thinner part of the proximal end 24 of the tool insert 13.

Figure 7:
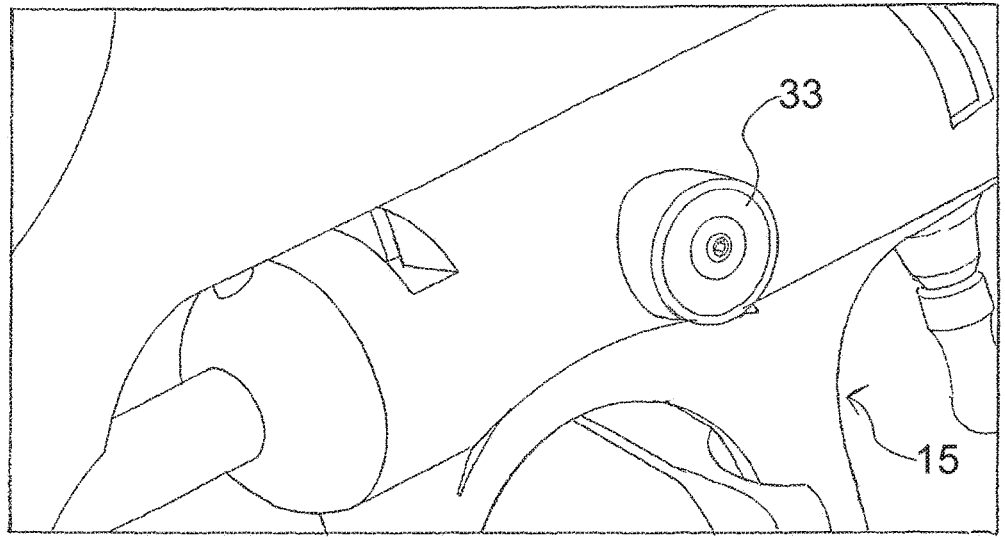
FIG. 7 is a close-up view of a part of the embodiment of FIG. 1.
Figure 8:
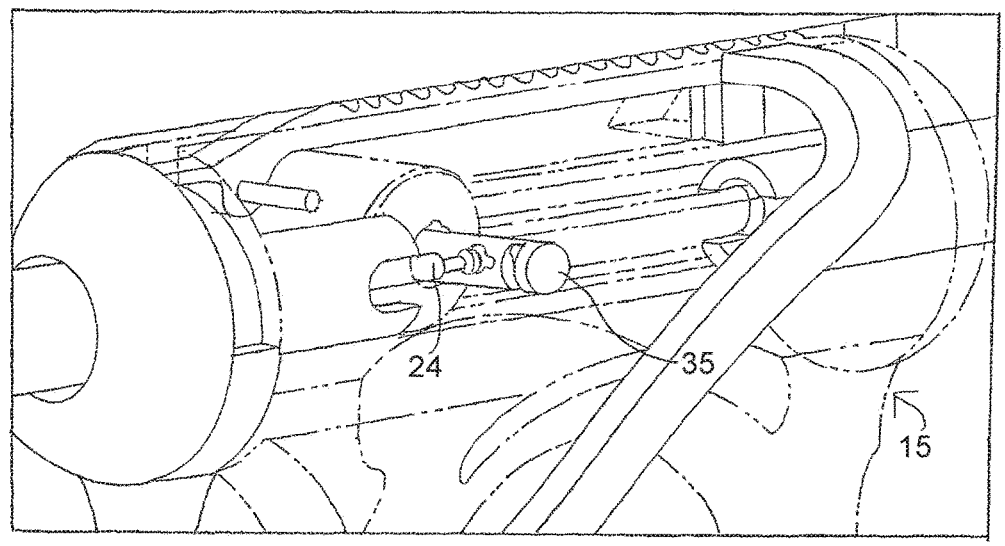
FIG. 8 is a close-up, cut-away view of a part of the embodiment of FIG. 1.

In the embodiment shown in FIGS. 5-11, the retaining member 35 is movable between an accepting position and a retaining position. In short, the retaining member moves perpendicularly to the longitudinal axis of the portion of the proximal end 24 of the tool insert 13 disposed in the actuation assembly 15. It moves between these two positions by pressing the button 33. FIGS. 7 and 8 show the actuation assembly when the retaining member has been moved into the accepting position. In FIG. 7, the button 33 is shown to be in a depressed position. FIG. 8 shows the retaining member 35 has been moved into the accepting position as a result of the depressing of the button 33. In the accepting position, the accepting portion 37 of the keyhole opening 36 is aligned with the path that the proximal end 24 of the tool insert 13 travels within the actuation assembly 15. This is shown in FIG. 8. In the accepting position, the tool insert 13 is slid through the accepting portion 37 of the retaining member 35 until the ball 25 is on the proximal side of the retaining member 35. In some embodiments, the proximal end 24 includes a stop portion 39 (shown in FIG. 3*b*) that is sized such that it will not pass through even the accepting portion 37 of the opening 36.

Figure 9:
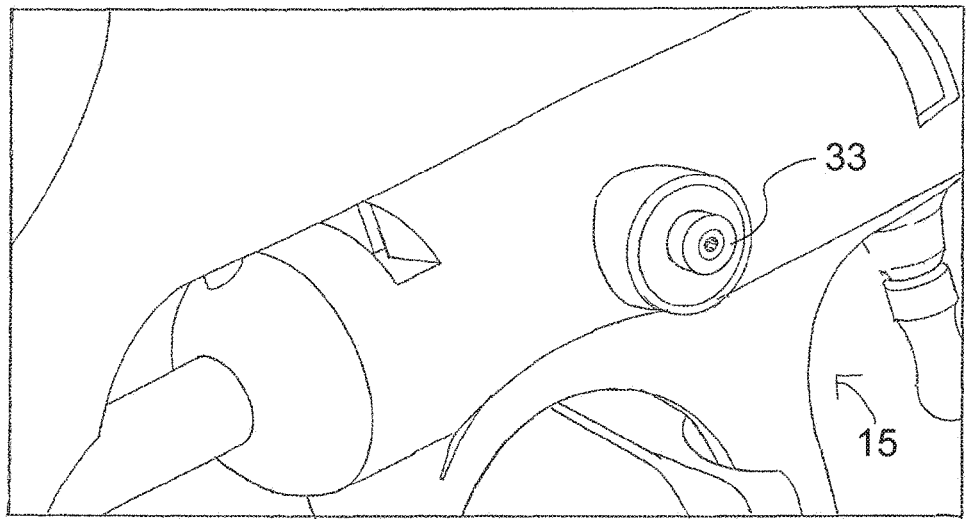
FIG. 9 is a close-up view of a part of the embodiment of FIG. 1.
Figure 10:
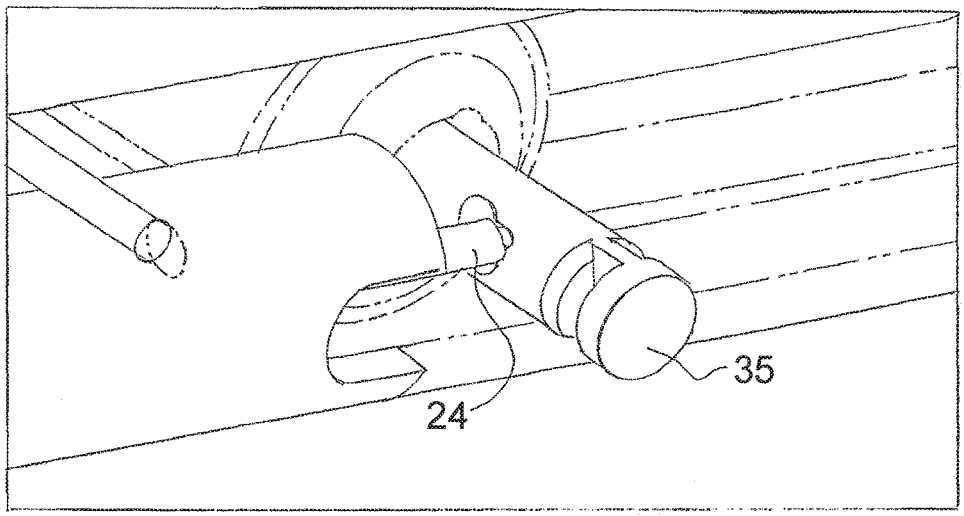
FIG. 10 is a close-up, cut-away view of a part of the embodiment of FIG. 1.

FIGS. 9 and 10 show the actuation assembly when the retaining member has been moved into the retaining position. In FIG. 9, the button 33 is shown in its undepressed state. Correspondingly, FIG. 10 shows the retaining member 35 in the retaining position, in which the retaining portion 38 is aligned with the path of travel of the proximal end 24 of the tool insert 13 within the actuation assembly 15. In this state, the retaining member 35 has captured the proximal end 24 of the tool insert, since the retaining portion 38 of the opening 36 is smaller than the ball 25. The proximal end 24 cannot move laterally with respect to the retaining member, because it is disposed in a chamber, typically cylindrically shaped, that prevents such lateral movement.

Figure 11:
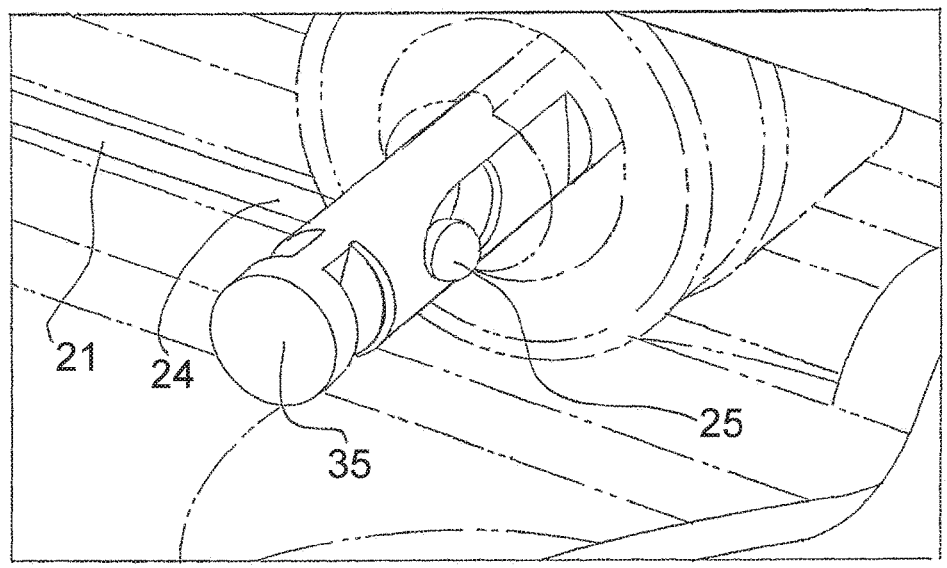
FIG. 11 is a close-up, cut-away view of a part of the embodiment of FIG. 1.

FIG. 11 shows an alternative view of the actuation assembly when the retaining member is in the retaining position with the ball 25 and the rest of the tool insert 13 in position.

Once the tool insert is disposed in the retaining member and the retaining member is in the retaining position, movement of the actuation assembly will cause actuation of the tool, such as jaw members 16*a* and 16*b*. The actuation assembly moves in the directions indicated by arrows 39 in FIG. 1. As described above, since the collar 23 and bearing 22 are fixed relative to the shaft 12, the longitudinal force imparted on the elongated member 21 by the actuation assembly 15 via the retaining member and ball 25 will cause the tool to bear against the bearing 22 and open and close.

Figure 13:
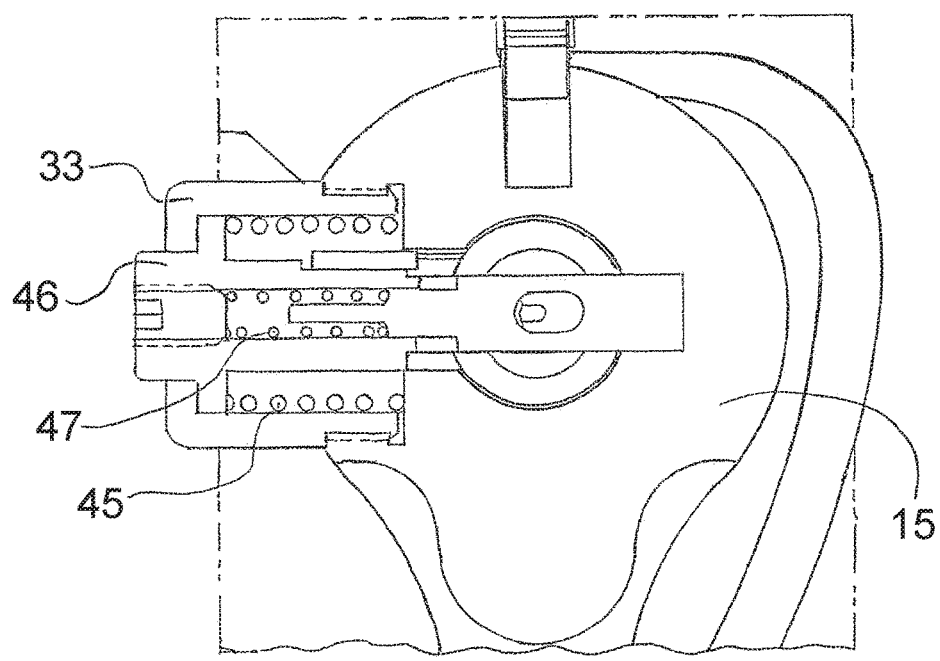
FIG. 13 is a cross-section view of a part of the embodiment of FIG. 1.

In the embodiment shown in the figures, the button 33 and retaining member 35 are biased in the retaining position. Accordingly, it is necessary for a user of the device to apply constant pressure to the button 33 to hold the retaining member 35 in the accepting position. Once such pressure is released, the retaining member 35 moves under the force of the bias back into the retaining position. The bias is supplied by a spring mechanism in some embodiments. FIG. 13 shows a cross-section view of portions of the actuation assembly 15 taken on a plane that is oriented perpendicularly to the longitudinal axis of the proximal end 24 of the tool insert 13. The section passes through the button 33 and retaining member 35. A first spring 45 exerts an outward force on a button element 46, such that the element 46 is pushed away from the assembly 15. A second spring 47 biases the retaining member 35 in the opposite direction: away from the element 46 and the rest of the button 33.

In some embodiments, the retaining member includes structure for holding itself in the accepting position against the bias even after the user has released pressure. Such a structure includes, for example, detents and protrusions similar to those utilized in retractable ball-point pens. In such embodiments, the user can press the button 33 once to move the retaining member into the accepting position and then press the button 33 a second time to move the retaining member back into the retaining position.

In other embodiments, alternative trigger-type structures are used instead of the actuation assembly 15. Such structures include, for example, a trigger that pivots with respect to the handle as opposed to the above described assembly which slides longitudinally.

Accordingly, to load a tool insert into the shaft and handle of the instrument, a user first feeds the elongated member into the distal end 20 of the shaft until the proximal end 24 of the insert reaches the retaining member 35. The user then moves the retaining member into the accepting position, moves the distal end of the insert through the accepting portion, and then causes the retaining member to move back into the retaining position. Subsequently or simultaneously, the user threads the collar onto the threaded surface 27 until it is seated on the distal end of the shaft. In this manner, the tool insert is securely disposed in the shaft and can be actuated using the handle of the instrument.

The present invention permits a user of the medical instrument to swap tool inserts quickly in order to use a variety of tool types without excessive duplication of equipment. A user can have an inventory of the different types of tools that could be needed for the surgical procedures at issue but have only two or a few of the shaft/handle assemblies. Swapping tools between the instruments is easy and does not compromise the effectiveness of the tools. Accordingly, it is possible to provide a kit that includes one or more handle/shaft assemblies along with a plurality of tool inserts each usable with the handle/shaft assemblies. This reduces the amount of equipment required to be purchased and maintained by the user, since a handle/shaft assembly is not required for each tool insert.

Figure 12A:
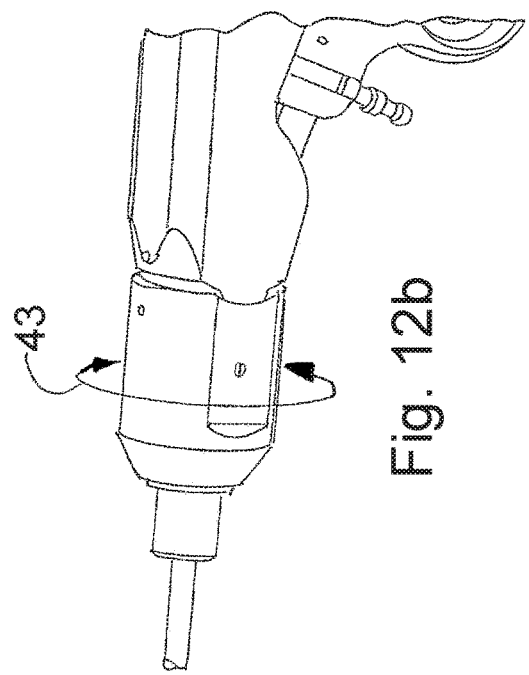
FIGS. 12a-12d are perspective views of the embodiment of FIG. 1.
Figure 12B:
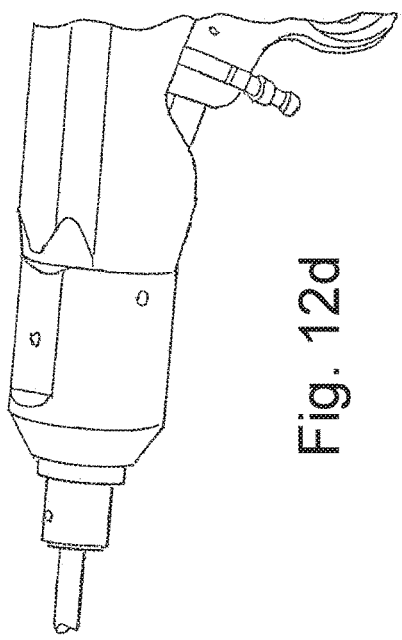
Figure 12C:
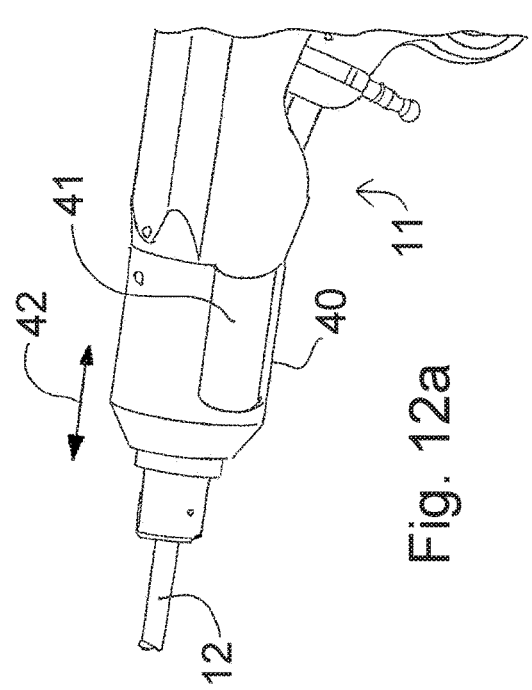
Figure 12D:
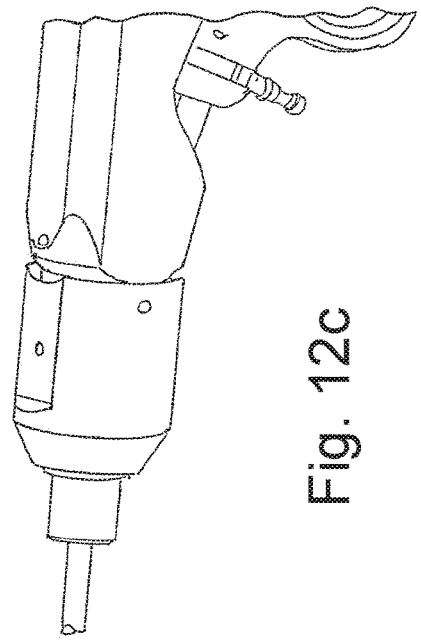

FIGS. 12*a-d* show an embodiment of the present invention that includes a feature by which the shaft 12 of the instrument (and, accordingly, any tool insert seated and secured in the instrument) is rotatable. At the point at which the shaft 12 meets the handle 11, a rotation member 40 is secured to the shaft 12. The rotation member 40 includes at least one flat portion 41 for gripping by a user. The rotation member 40 is slideable relative to the shaft 12 along the direction of the longitudinal axis of the member 40, as shown by the arrow 42 shown in FIG. 12*a*, which coincides with the longitudinal axis of the shaft 12 in that region. It is slideable between a locking position and a rotating position. The locking position is shown in FIGS. 12*a* and 12*d* and the rotating position is shown FIGS. 12*b* and 12*c*. Although the member 40 is slideable relative to the shaft 12, it is fixed in rotation with respect to the shaft. Accordingly, when the member 40 is moved into the rotating position shown in FIG. 12*b*, it can be rotated as indicated by arrow 43 into the position shown in FIG. 12*c*. This movement causes the entire shaft 12, as well as any tool insert that is secured in the shaft, to also rotate. The tool insert will be caused to also rotate by virtue of the engagement of the protrusions on the tool insert bearing with the slots on the distal end of the shaft as discussed above. Once the shaft has been rotated into the desired position, the member 40 is moved back into the locking position shown in FIG. 12*d* in which further rotation of the shaft is prevented. In some embodiments, the member 40 is biased into the locking position such that it will automatically return to that position from the rotating position once the user releases the member 40.

In the embodiment shown in FIG. 12, the shaft is rotatable between discrete positions that are 90° apart. In other embodiments, different intervals are used between discrete positions.

Although the invention has been described with reference to particular arrangements of parts, features and the like, these are not intended to exhaust all possible arrangements or features, and indeed many other modifications and variations will be ascertainable to those of skill in the art.

What is claimed is:

1. A medical instrument, comprising:
   a shaft comprising a threaded portion on a distal end of the shaft and at least one slot on the distal end of the shaft;
   a handle connected to the shaft;
   a tool insert receivable in the shaft, comprising:
      a tool portion including a bearing with at least one protrusion for engagement with the at least one slot to prevent rotation of the tool portion relative to the shaft;
      a collar on a proximal side of the bearing and rotatable relative to the tool portion, the collar comprising threads that correspond to the threaded portion of the shaft; and
      an elongated member for engagement with the handle for actuation of the tool portion.

2. The medical instrument of claim 1, wherein the shaft further comprises two slots formed between four protrusions on the distal end of the shaft.

3. The medical instrument of claim 2, further comprising that each protrusion includes at least one surface inclined at an angle relative to the longitudinal axis of the shaft at its distal end.

4. The medical instrument of claim 1, wherein the tool insert further comprises a ball attached at a proximal end of the elongated member for engaging with the handle and the handle further comprising an opening for engaging with the ball.

5. The medical instrument of claim 4, wherein the opening is a keyhole opening for accepting and retaining the ball that is moveable between a retaining position and an accepting position.

6. The medical instrument of claim 5, wherein the handle further comprises an actuation assembly which receives a proximal end of the elongated member and in which the keyhole opening is disposed, and wherein the keyhole opening is moveable in a direction perpendicular to the longitudinal axis of the portion of the elongated member disposed in the actuation assembly.

7. The medical instrument of claim 6, further comprising that the keyhole opening is biased in the retaining position.

8. The medical instrument of claim 1, wherein the shaft further comprises a rotation member on its proximal end for rotating the shaft and the tool insert relative to the handle, the rotation member being moveable along the longitudinal axis of the shaft at the portion of the shaft that is connected to the handle.

9. A medical instrument, comprising:
   a shaft comprising a threaded portion on a distal end of the shaft and at least one slot on the distal end of the shaft;
   a handle connected to the shaft, comprising:
      a retaining member comprising an opening and being moveable between a retaining position and an accepting position;
   a tool insert receivable in the shaft, comprising:
      a tool portion including a bearing with at least one protrusion for engagement with the at least one slot to prevent rotation of the tool portion relative to the shaft;
      an elongated member including a ball on a proximal end thereof for engaging with the opening; and
      a collar on a proximal side of the tool portion and rotatable relative to the tool portion, the collar comprising threads that correspond to the threaded portion of the shaft;
   wherein the retaining member permits the handle to exert force on the elongated member along a longitudinal axis thereof for actuation of the tool portion.

10. The medical instrument of claim 9, wherein the handle further comprises an actuation assembly in which the retaining member is disposed and which receives the proximal end of the elongated member and wherein the retaining member is moveable in a direction perpendicular to the longitudinal axis of the portion of the elongated member disposed in the actuation assembly.

11. The medical instrument of claim 10, wherein the opening is a keyhole opening including an accepting portion sized larger than the ball and a retaining portion sized smaller than the ball.

12. The medical instrument of claim 11, wherein when the retaining member is in the retaining position, the retaining portion of the opening is aligned with the longitudinal axis of the portion of the elongated member disposed in the actuation assembly and wherein when the retaining member is in the accepting position, the accepting portion is aligned with the longitudinal axis of the portion of the elongated member disposed in the actuation assembly.

13. The medical instrument of claim 12, wherein the retaining member is a rod and is biased in the retaining position.

14. The medical instrument of claim 9, wherein the shaft further comprises two slots formed between four protrusions on the distal end of the shaft.

15. A medical instrument, comprising:
   a shaft comprising a threaded portion on a distal end of the shaft and at least one slot on the distal end of the shaft;
   a handle connected to said shaft, comprising:
      a retaining member comprising an opening and being moveable between a retaining position and an accepting position;
   a tool insert receivable in the shaft, comprising:
      a tool portion including a bearing with at least one protrusion for engagement with the at least one slot to prevent rotation of the tool portion relative to the shaft;
      a collar on a proximal side of the tool portion and rotatable relative to the tool portion, the collar comprising threads that correspond to the threaded portion of the shaft; and
      an elongated member including a ball on a proximal end thereof for engaging with the opening;
   wherein the retaining member permits the handle to exert force on the elongated member along a longitudinal axis thereof for actuation of the tool portion.

16. The medical instrument of claim 15, wherein the shaft further comprises two slots formed between four protrusions on the distal end of the shaft.

17. The medical instrument of claim 16, further comprising that each protrusion includes at least one surface inclined at an angle relative to the longitudinal axis of the shaft at its distal end.

18. The medical instrument of claim 15, wherein the handle further comprises an actuation assembly in which the retaining member is disposed and which receives the proximal end of the elongated member and wherein the retaining member is moveable in a direction perpendicular to the longitudinal axis of the portion of the elongated member disposed in the actuation assembly.

19. The medical instrument of claim 18, wherein the opening is a keyhole opening including an accepting portion sized larger than the ball and a retaining portion sized smaller than the ball.

20. The medical instrument of claim 19, wherein when the retaining member is in the retaining position, the retaining portion of the opening is aligned with the longitudinal axis of the portion of the elongated member disposed in the actuation assembly and wherein when the retaining member is in the accepting position, the accepting portion is aligned with the longitudinal axis of the portion of the elongated member disposed in the actuation assembly.

21. The medical instrument of claim 20, wherein the retaining member is a rod and is biased in the retaining position.

\* \* \* \* \*